US012527679B1

(12) United States Patent
Shepherd et al.

(10) Patent No.: US 12,527,679 B1
(45) Date of Patent: Jan. 20, 2026

(54) HAND IMMOBILIZER SYSTEM

(71) Applicant: Instrument Specialists, Inc., Boerne, TX (US)

(72) Inventors: Casey Shepherd, Boerne, TX (US); Chris Harrelson, Boerne, TX (US)

(*) Notice: Subject to any disclaimer, the term of this patent is extended or adjusted under 35 U.S.C. 154(b) by 29 days.

(21) Appl. No.: 17/446,075

(22) Filed: Aug. 26, 2021

Related U.S. Application Data

(60) Provisional application No. 63/070,563, filed on Aug. 26, 2020.

(51) Int. Cl.
*A61F 5/058* (2006.01)

(52) U.S. Cl.
CPC ...... *A61F 5/05866* (2013.01); *A61F 5/05875* (2013.01)

(58) Field of Classification Search
CPC .... A61F 5/05866; A61F 5/0118; A61F 13/00; A61F 13/00051; A61F 13/00059; A61F 13/00085; A61F 13/00089; A61F 13/15; A61F 13/02; A61F 13/023; A61F 13/0243; A61F 13/0266; A61F 13/42; A61F 2013/00153; A61F 2013/15008; A61F 2013/421; A61F 2013/422; A61F 2013/423; A61F 2013/444; A61F 5/013; A61F 5/05858; A61F 5/05875; A61F 5/10; A61F 5/3723; A61L 15/24; A61L 15/56; A61B 5/145; A61B 5/44; A61B 5/441; A61B 5/445; G16H 50/00; A41D 19/01582; A41D 19/01588
See application file for complete search history.

(56) References Cited

U.S. PATENT DOCUMENTS 1,144,103 A * 6/1915 Brant .................. A61F 5/05875 602/22
3,203,006 A * 8/1965 Shirley ................ A63B 71/148 473/59
3,692,022 A * 9/1972 Ewing ................. A61F 5/05875 602/22
4,204,533 A * 5/1980 Forster ...................... A61F 5/37 602/22
4,781,178 A * 11/1988 Gordon ................. A61F 5/0118 602/22
5,143,505 A * 9/1992 Burdea .................... B25J 13/02 244/234
5,560,375 A * 10/1996 Kabanek ............... A61F 5/3761 128/878

(Continued)

OTHER PUBLICATIONS

McKesson, Surgical Hand Immobilizer Framer Malleable Lead Left or Right Hand Gray Standard, https://mms.mckesson.com/product/634461/Miltex-PM-4480 (accessed May 2020).

*Primary Examiner* — Alireza Nia
*Assistant Examiner* — Gina McCarthy
(74) *Attorney, Agent, or Firm* — Werner IP Law, P.C.

(57) ABSTRACT

A hand immobilizer system which has a body in the general shape of the hand, including a portion shaped like the metacarpus of the hand and laterally outwardly extending portions or digits shaped like the fingers of the hand. The hand immobilizer further comprises a pliable piece of material, e.g., aluminum which is either formed or can be formed so as to at least partially encircle the finger of the patient and the digit of the hand immobilizer on which the finger rests.

8 Claims, 6 Drawing Sheets

(56) References Cited

U.S. PATENT DOCUMENTS

| | | | | |
|---|---|---|---|---|
| 5,855,209 | A | 1/1999 | Hernandez et al. | |
| 6,561,995 | B1 * | 5/2003 | Thibodo, Jr. | A61F 5/0118 128/880 |
| 7,856,670 | B1 * | 12/2010 | Hazuga | A63B 23/16 2/163 |
| 2012/0289877 | A1 * | 11/2012 | Hegland | A61F 5/013 602/22 |
| 2015/0068534 | A1 | 3/2015 | Lubbers et al. | |
| 2021/0267786 | A1 * | 9/2021 | Kitay | A61F 5/3761 |
| 2021/0307950 | A1 * | 10/2021 | Perelman | A61F 5/05875 |

* cited by examiner

HAND IMMOBILIZER SYSTEM

FIELD OF THE INVENTION

The present invention relates to hand immobilizers used in surgical settings.

BACKGROUND OF THE INVENTION

Hand immobilizers used during surgery either on the hand or some other part of the body are disclosed for example in U.S. Pat. Nos. 5,560,375 and 5,855,209 (collectively Hand Immobilizer Patents), both of which are incorporated herein by reference for all purposes.

As can be seen from the Hand Immobilizer Patents, the hand immobilizers do not have digit restraints other than on the ends of the digits, those restraints being bendable, as shown in the Hand Immobilizer Patents, over the tips of the patient's finger. However, there are instances wherein a digit restraint which could be selectively, releasably positioned along the length of the digit would be desirable. In this regard, a surgical hand immobilizer marketed by Mckesson Medical-Surgical, Inc. (Mckesson) has tabs monolithically formed with the Mckesson immobilizer, the tabs extending laterally outwardly from some of the digits. The Mckesson immobilizer suffers from the disadvantage that the tabs, since they are monolithic with the hand immobilizer, are not selectively, releasably positionable along the length of the digit.

SUMMARY OF THE INVENTION

In one aspect, the present invention relates to a hand immobilizer system wherein one or more fingers of the hand can be gripped, together with the digit of a hand immobilizer, at a desired axial location along the length of the finger.

In another aspect, the present invention relates to a hand immobilizer system wherein a clip which is at least partially deformable can be selectively, releasably positioned in at least partially surrounding relationship to at least one of the digits of the hand immobilizer and the finger of the patient.

These and further features and advantages of the present invention will become apparent from the following detailed description, wherein reference is made to the figures in the accompanying drawings.

FIG. B is a perspective view of another embodiment of the present invention wherein the clip is spiral or helically shaped.

Figure 5:
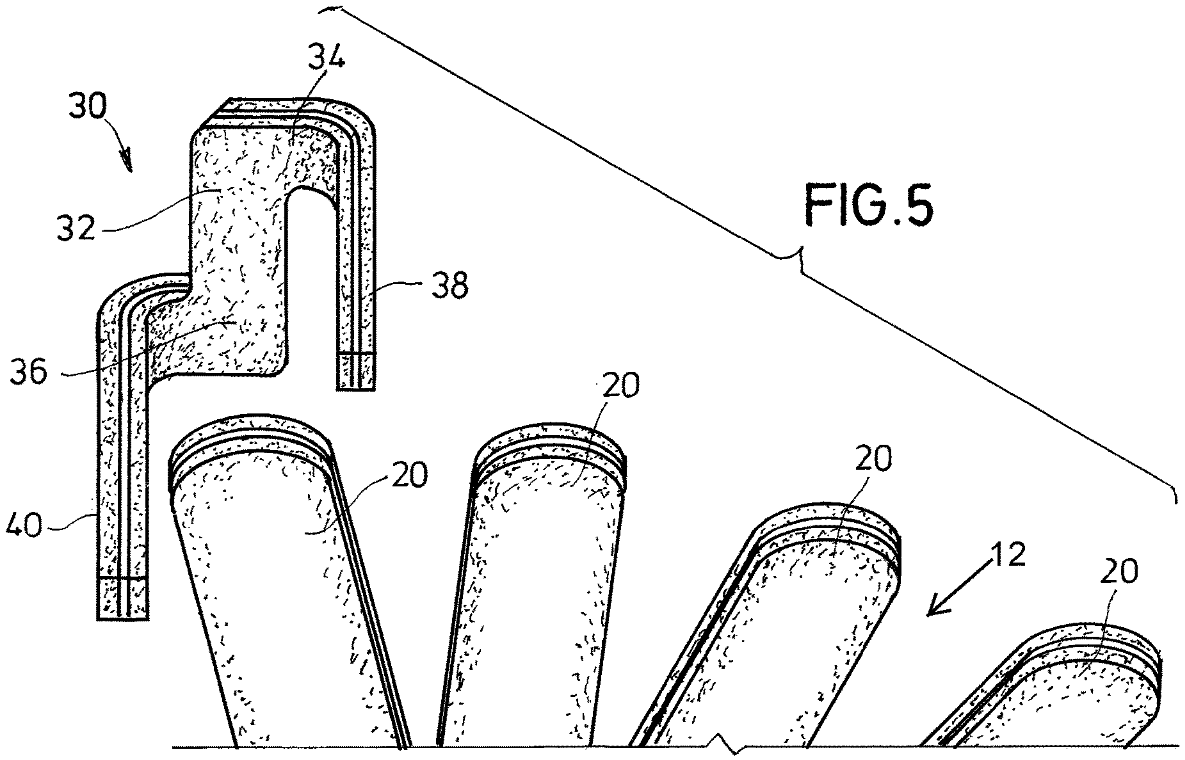
FIG. 5 is a perspective view of another embodiment of the present invention wherein the clip has a web which connects two axially spaced legs whereby the clip can at least partially encircle two axially spaced locations on a digit of the hand immobilizer.
Figure 6:
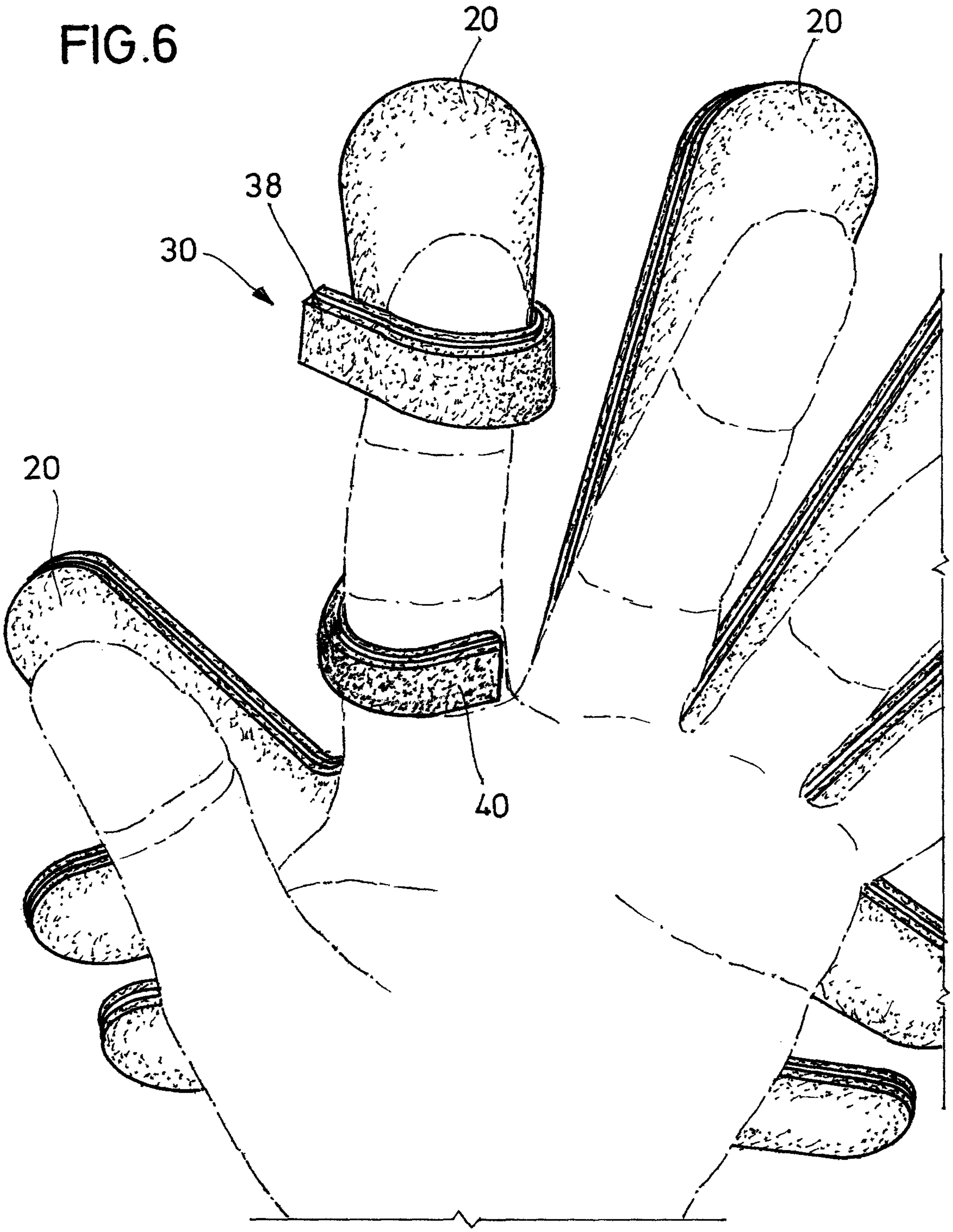

FIG. 6 is a perspective view showing the clip of FIG. 5 in surrounding relationship to a patient's fingers and the corresponding digit of the hand immobilizer.

Figure 7A:
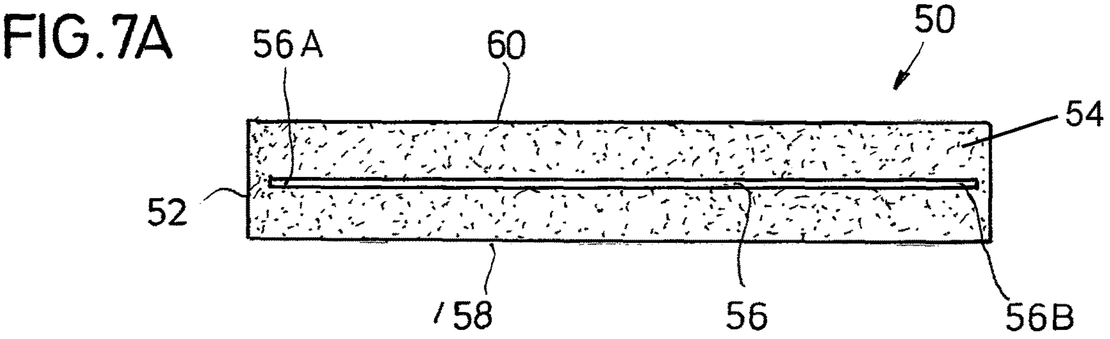

FIG. 7A is a side elevational view of a clip according to one embodiment of the hand immobilizer system of the present invention.

Figure 7B:
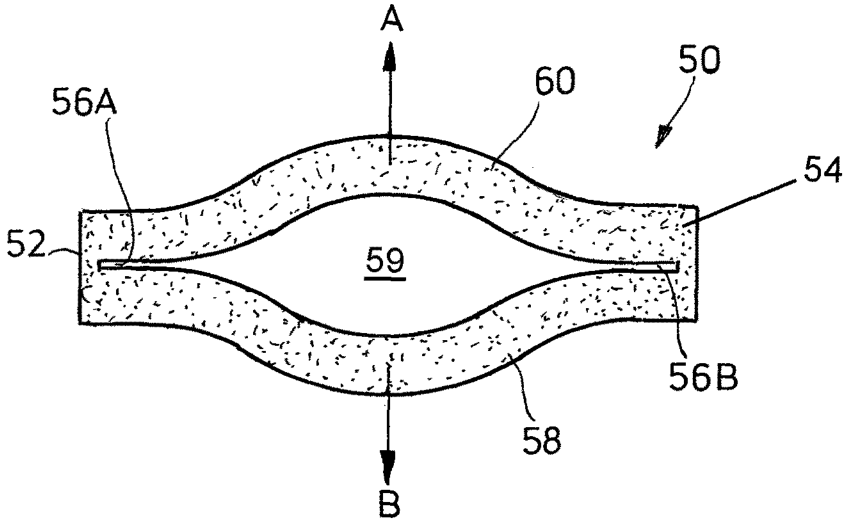

FIG. 7B is a view similar to FIG. 7A but showing the clip spread and in a position to be slipped over the finger of a patient and the corresponding digit of the hand immobilizer.

Figure 7C:
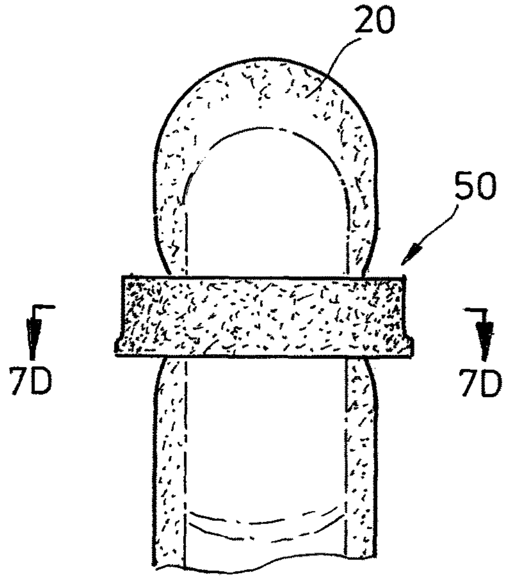

FIG. 7C shows the clip of FIG. 7B positioned around a patient's finger and a corresponding digit of the hand immobilizer.

Figure 7D:
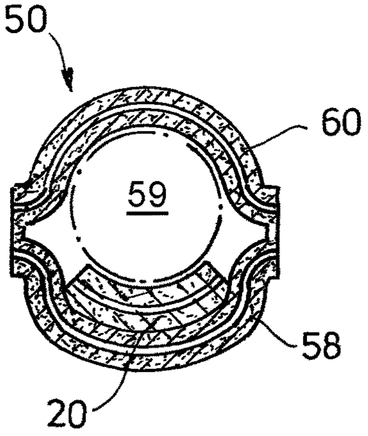

FIG. 7D is a cross-sectional view taken along the lines 7D-7D of FIG. 7C.

DETAILED DESCRIPTION OF PREFERRED EMBODIMENTS

A hand immobilizer system of the present invention comprises a hand immobilizer and a separate clip which is adapted to be selectively and releasably positioned in at least partially surrounding relationship to at least one of the digits of the hand immobilizer as well as the fingers of a patient on that digit.

Figure 1:
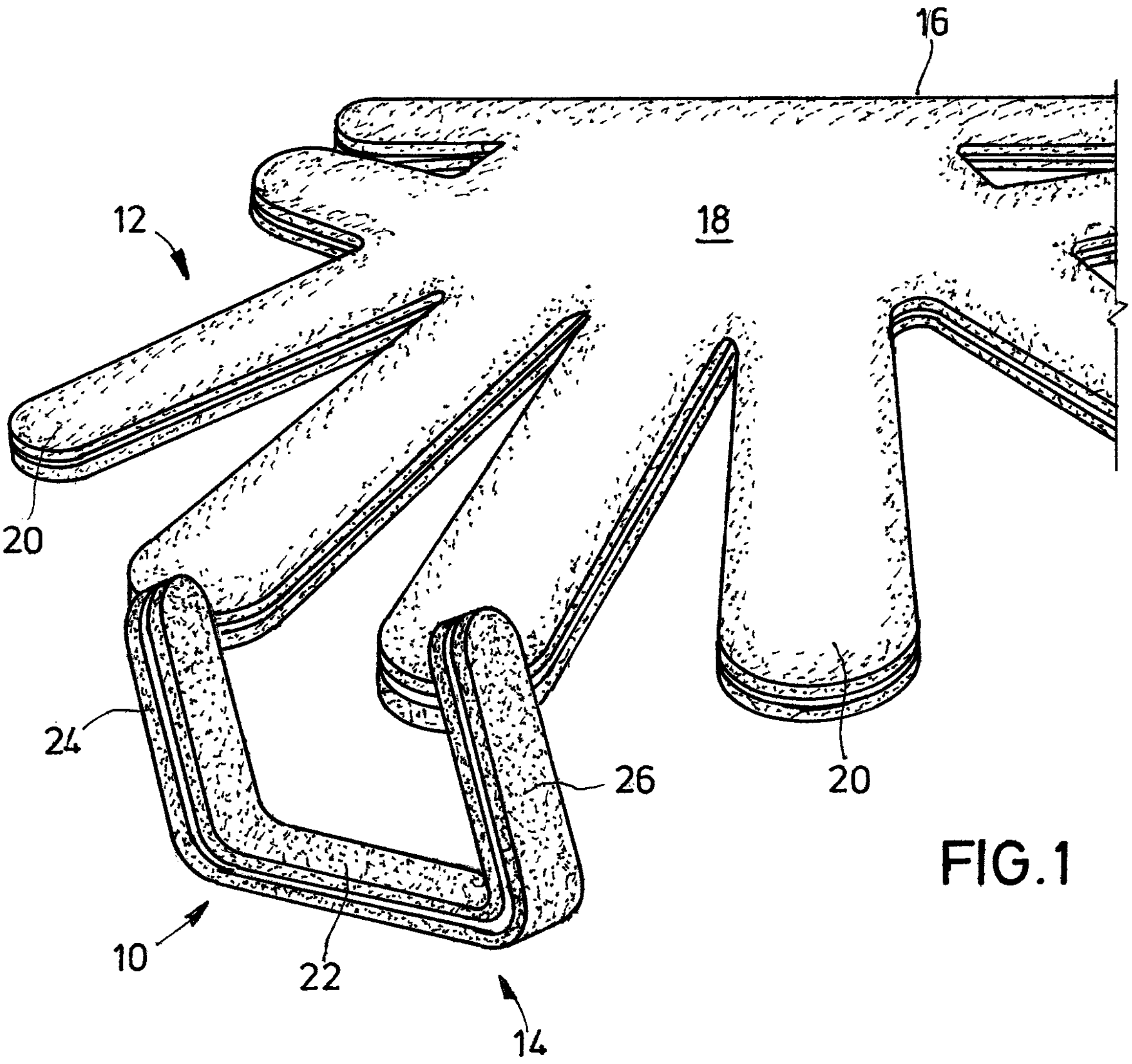
FIG. 1 is a perspective view of one embodiment of the system of the present invention showing a clip and a hand immobilizer.

Referring first to FIG. 1, there is shown one embodiment of the hand immobilizer system (HIS). The HIS of FIG. 1, shown generally as 10 comprises a hand immobilizer shown generally as 12 and a clip shown generally as 14.

Hand immobilizer 12 comprises a plate like body 16 having a main portion 18 generally corresponding to the main portion of a human hand, i.e., the metacarpus. Extending laterally outwardly from the metacarpus portion or main body portion 18 are digits 20 corresponding to the respective shapes of the fingers of the hand. As can be seen, the digits 20 are splayed outwardly from main body portion 18 so as to conform to the shape of a human hand when the fingers are spread.

Figure 1A:
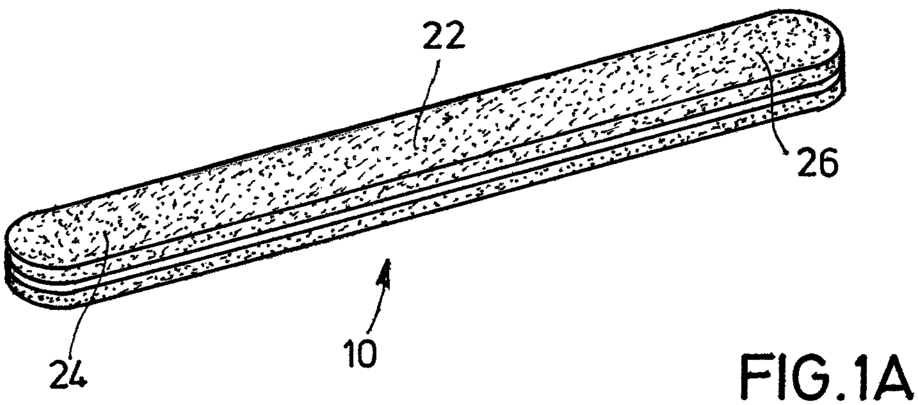
FIG. 1A is a perspective view of the clip used in the embodiment of FIG. 1.

Clip 14 as shown in the embodiment of FIG. 1 is generally U-shaped in elevation having a bridge 22 from which depend legs 24 and 26. As seen in FIG. 1A, the clip 14 can be formed form an elongate, generally flat bar.

Figure 2:
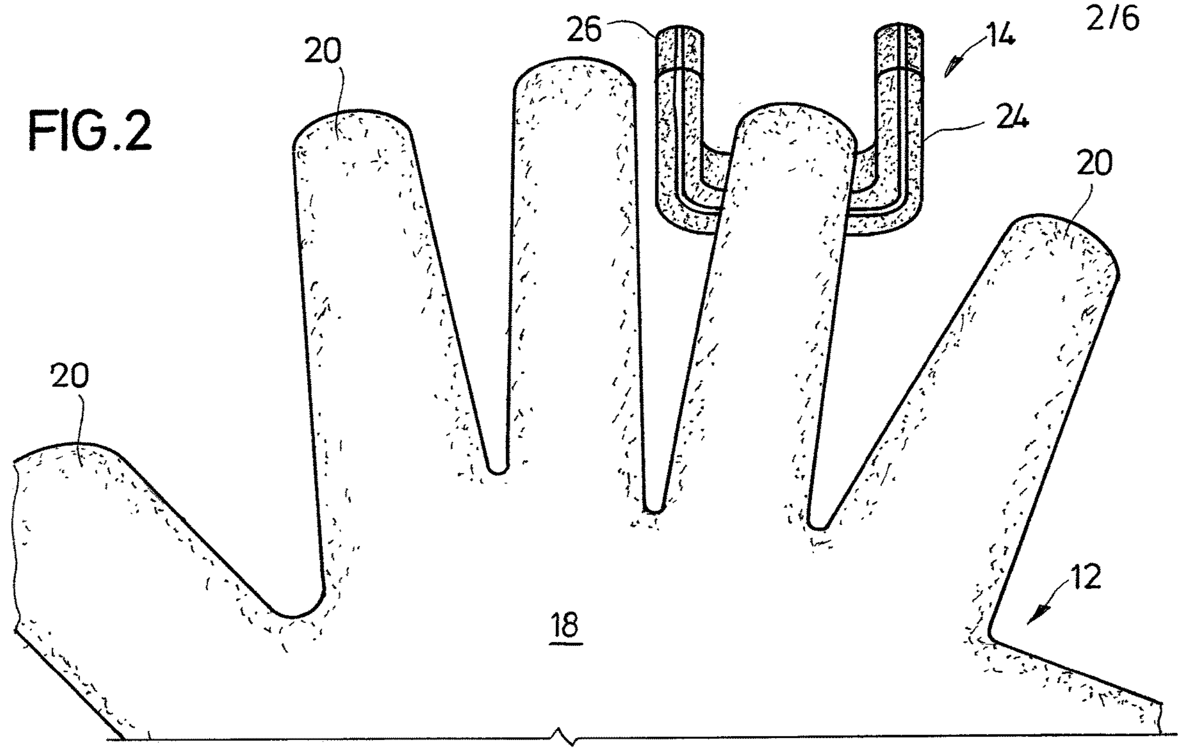
FIG. 2 is a view similar to FIG. 1 but showing the clip partially positioned on a digit of a hand immobilizer.
Figure 3:
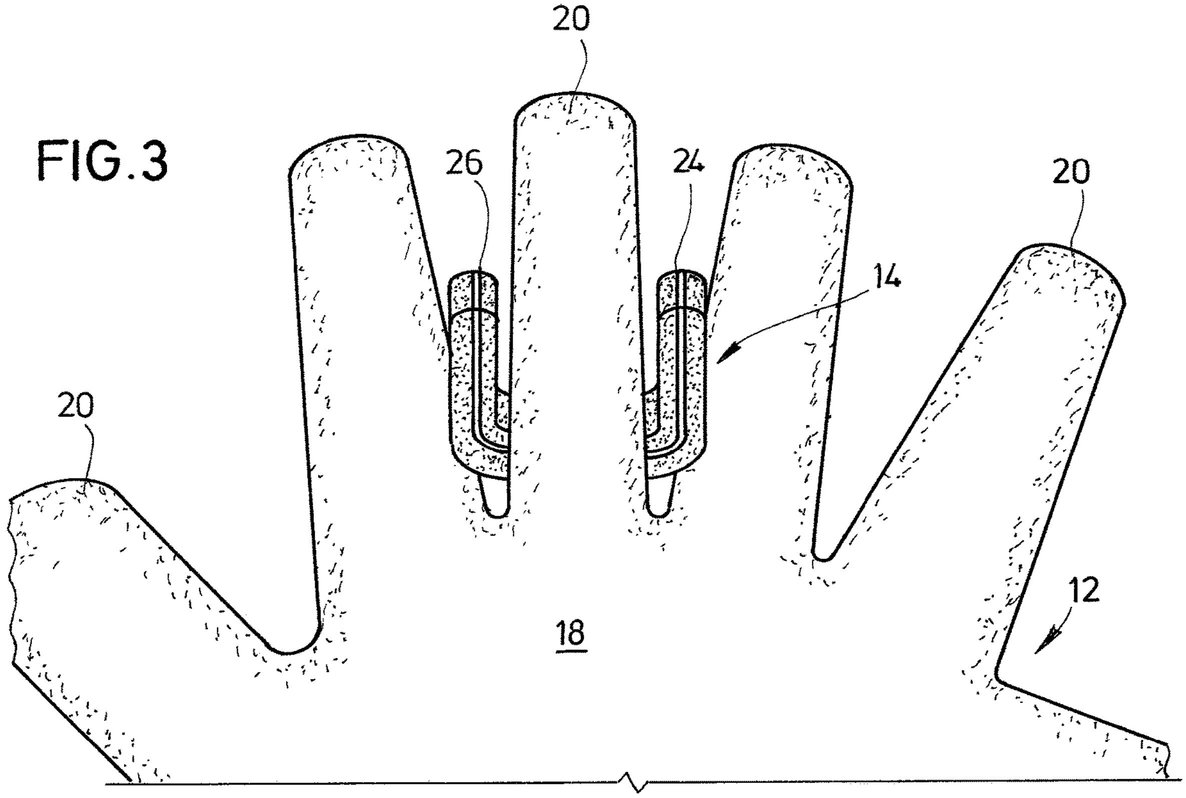
FIG. 3 is a view similar to FIG. 2 but with the clip partially positioned on a different digit of the hand immobilizer.

Referring now to FIG. 2, the HIS 10 of FIG. 1 is shown with clip 14 positioned adjacent one of the digits 20. As seen the bridge 22 of the clip 14 underlies the digit 20 with legs 24 and 26 positioned on either side of the digit 20. FIG. 3 is substantially the same as FIG. 2 with the exception that the clip 14 of. FIG. 3 is shown positioned partially surrounding a digit on the hand immobilizer.

Figure 4:
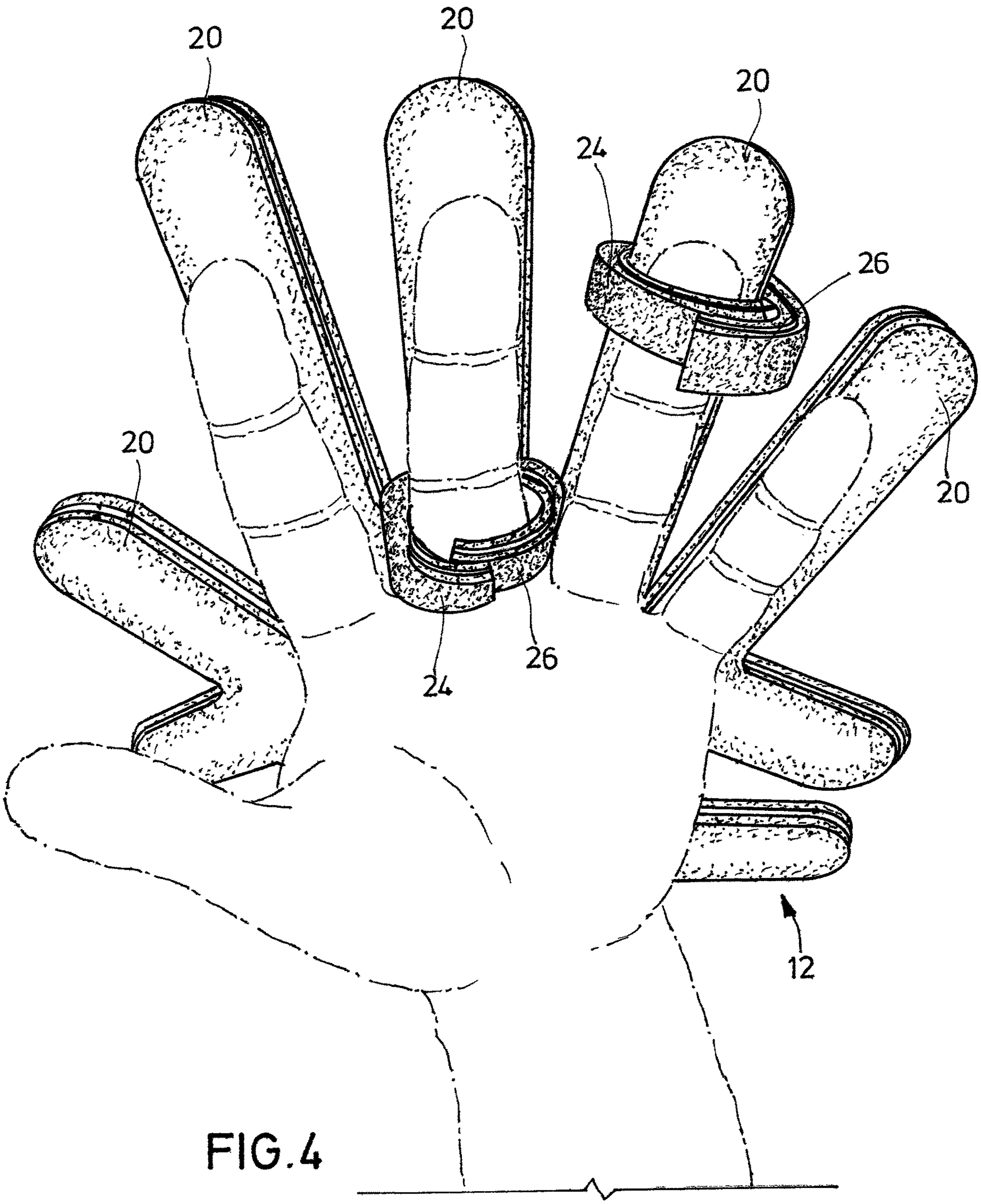
FIG. 4 shows the hand immobilizer of the present invention wherein two clips are positioned on two different digits and in surrounding relationship to the fingers of a patient and the corresponding digits of the hand immobilizer.

FIG. 4 is a perspective view of a patient's hand and two of the digits on the hand immobilizer and the clips of FIG. 1A being deformed or bent to encircle the fingers of the patient and the digits 20 of the hand immobilizer 12 on which the fingers rest.

FIG. 5 shows another embodiment of the HIS of the present invention, which comprises a hand immobilizer 12, and a clip 30 comprised of a web portion 32 having end portion 34 and 36 at opposed ends of web 32. Deformable gripping legs 38 and 40 from end portions 34 and 36, respectively. Clip 30 is an example of how the clips of the HIS of the present invention could be made wherein only a portion of a clip is deformable or bendable. In this regard, it will be apparent that web portion 32 as well as extensions 34 and 36 could be made from a less deformable or nondeformable material while the legs or gripping portions 38 and 40 are made of a bendable, deformable material.

Figure 5A:
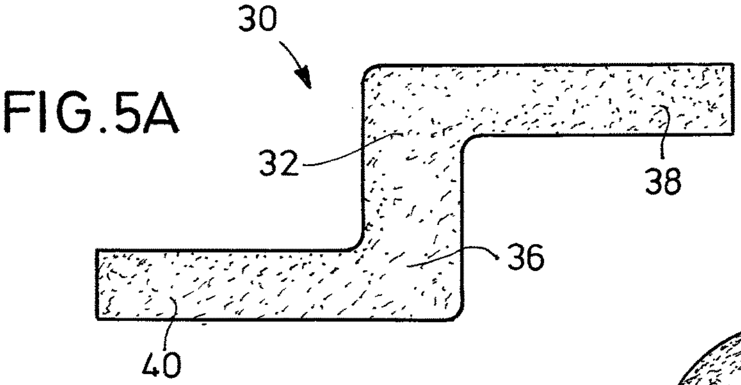
FIG. 5A is a top plan view of the clip shown in FIG. 5.
Figure 5B:
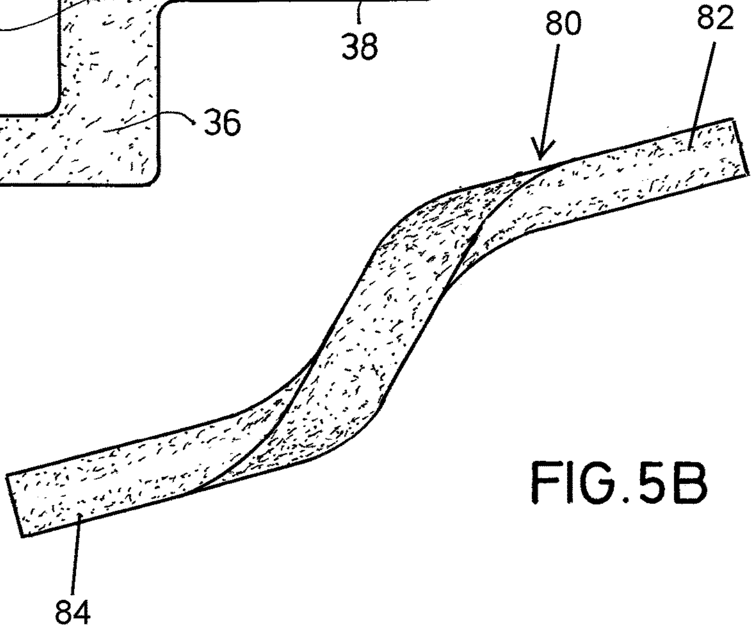

FIG. 5A shows a planar view of clip 30 prior to being deformed around a digit and finger as shown in FIG. 6

FIG. B shows a clip 80 having a helical configuration which effectively forms a tunnel through which a finger of a patient and corresponding digit on the hand immobilizer can extend.

The clip 80 is in the shape of a helical coil having an open core 59 and axially extending legs 82 and 84 such that it could be slipped over the tip of a patient's finger and digit 20 of the hand immobilizer and then the free ends or legs 82 and 84 of the coil shaped clip 80 deformed around the combined finger/digit. Depending on the axial length of such a coil shaped clip 80, the clip 80 would serve the purpose, much like clip 30, of clamping a finger of a patient at two axially spaced locations on the digit 20 of the hand immobilizer 12.

FIG. 6 shows an embodiment of the HIS of the present invention wherein a patient's hand is on a hand immobilizer 12, one of the fingers of the patient's hand being clamped to a digit 20 by the clip 30 shown in FIG. 5A.

Turning to FIGS. 7A-7D, there is shown an elongate generally rectangular strip or bar 50 of deformable metal having a first end 52, a second end 54, a first side 58, and a second side 60. There is a slit 56 running longitudinally along bar 50, slit 56 having a first end 56A proximate first end 52 and a second end 56B proximate second end 54. As can be seen, slit 56 results in there being side sections 58 and 60. As seen in FIG. 7B, if side section 60 is moved in the direction of arrow A and side second 58 is moved in the direction of arrow B, ends 52 and 54 and the spread side sections 58 and 60 will cooperate to form a tunnel 59 as shown in FIG. 7A through which a digit of the hand immobilizer and a finger of a patient resting on that digit can pass. Since the clip 50 is deformable, the spread side sections 58 and 60 can then be urged into gripping contact with the finger of the patient as well as the digit of the hand immobilizer on which the finger rests. FIGS. 7C and 7D show the clip 60 in surrounding relationship to a patient's finger and a digit of the hand immobilizer.

It will be appreciated from the above description and drawings that the clip forming part of the HIS of the present invention can take many shapes. For one, it can just be a straight member or bar which is then bent into a band to at least partially encircle a finger of a hand positioned on a digit 20 of the hand immobilizer 12.

The HIS 10 could be constructed of various materials in accordance with the teachings of the Hand Immobilizer Patents. Thus, as taught in those patents, aluminum is one preferred material that can be employed. However, the HIS 10 could also be made of lead or other pliable/deformable materials, including certain composites. As shown the clip can comprise a laminated structure with a central metallic linkable portion is overlaid with suitable padding as shown and described above.

The clips of the present invention are constructed at least in part of a pliable, bendable, or deformable material so as to be formable into a band which at least partially encirlces the finger of the user and the digit on which that finger rests. Thus, by way of example, the clips can be made of strips of aluminum, lead or other composites that are deformable, bendable, or pliable, or can be made of such materials but in preformed shapes such as described above. Also the clips can have padding on a portion of one side, one side only, or on both sides.

The HIS of the present invention is an improvement over prior art hand immobilizer systems in that it has greater flexibility in terms of where one or more fingers positioned on the hand immobilizer body 12 can be gripped relative to the corresponding digit of the hand immobilizer in virtually any location along the axial extent of the finger. Two clips could be placed on a single finger and digit, one above the knuckle and one below the knuckle. Further, some of the clip designs can act like two clips in the sense that a single clip can have gripping portions which are axially spaced along the digit of the hand immobilizer as well as the finger of the patient.

One advantage of the system of the present invention is that the clips can be used with any hand immobilizer allowing the surgeon to choose a desired hand immobilizer and then use the clips for precise positioning.

An additional feature is that the clips can be easily made by metal stamping, laser cutting or other such techniques that do not require any expensive machining.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A hand immobilizer system for use in surgical settings, comprising: a plate-shaped body having a general hand shape, said body having a main portion shaped to a metacarpus of said hand shape and five laterally outwardly extending digits shaped to respective fingers of said hand shape; and a separate clip comprised of metal and adapted to be selectively and releasably positioned in at least partially surrounding relationship to at least one of said digits, said clip being selectively movable to different points along an entire length of said digits, said clip having at least a portion which is deformable such that it is able to be at least partially wrapped around a patient's finger and hold said finger in a desired position against a respective digit of said hand immobilizer such that said patient's hand is maintained in position for surgery.

2. The hand immobilizer system of claim 1, wherein said clip prior to use comprises an elongate flat bar.

3. The hand immobilizer system of claim 2 wherein said clip is formed into a band.

4. The hand immobilizer system of claim 1, wherein the clip comprises a central web having a first end and a second end, prior to said clip being in use there being a first leg extending laterally outwardly in a first direction from said web adjacent said first end, and a second leg extending laterally outwardly in a second, opposite direction adjacent the second end, said first and second legs being deformable such that they are able to grip a patient's finger on a respective digit in two axially spaced locations, prior to said clip being in use, said central web and said first and second legs are coplanar and the lengths of said first and second legs are perpendicular to the length of said central web.

5. The hand immobilizer system of claim 1, wherein prior to use the clip comprises a central portion which spirals along its length and first and second axially extending legs extending from said central portion.

6. The hand immobilizer system of claim 1, wherein said clip prior to use comprises a flat metal bar having a first end and a second end, there being a longitudinal slit between said first and second ends, said slit forming a first lateral section and a second lateral section, said lateral sections being laterally deformable away from one another to form a tunnel for receiving a digit of the hand immobilizer system and a finger of a patient.

7. The hand immobilizer system of claim 1, wherein said clip is adapted to be selectively and releasably positioned in surrounding relationship to said digit and a finger positioned on said digit.

8. The hand immobilizer system of claim 1, wherein said plate-shaped body is formed from aluminum or lead.

* * * * *